US005545177A

United States Patent [19]

Coseo

[11] Patent Number: 5,545,177

[45] Date of Patent: Aug. 13, 1996

[54] APPARATUS FOR APPLYING ACUPRESSURE

[76] Inventor: Marc C. Coseo, 1 Harbor St., Manchester, Mass. 01944

[21] Appl. No.: 294,998

[22] Filed: Aug. 24, 1994

[51] Int. Cl.[6] .................... A61F 5/32; A61F 5/00; A61H 39/00; A61B 17/54

[52] U.S. Cl. .................... 606/204; 606/239; 606/238; 601/107; 601/117; 601/134

[58] Field of Search .................... 606/204, 201, 606/237, 238, 239, 240, 241, 242, 243, 244, 245; 601/117, 116, 115, 107, 108, 110, 111, 134, 97, 98, 84

[56] References Cited

U.S. PATENT DOCUMENTS

| | | | |
|---|---|---|---|
| 2,461,102 | 2/1949 | Ackerman | 601/117 |
| 2,714,381 | 8/1955 | Corley et al. | 601/134 |
| 3,403,674 | 10/1968 | Alimanestiano | 128/61 |
| 3,799,155 | 3/1974 | Gerlich | 128/44 |
| 4,037,590 | 7/1977 | Dohring et al. | 128/24 |
| 4,352,491 | 10/1982 | Bellia | 272/144 |
| 4,520,798 | 6/1985 | Lewis | 128/24 |
| 4,662,363 | 5/1987 | Romano et al. | 128/60 |
| 4,716,898 | 1/1988 | Chauve et al. | 128/329 |
| 4,850,343 | 7/1989 | Scott | 606/245 |
| 4,924,859 | 1/1990 | Pajevic | 128/52 |
| 4,944,747 | 7/1990 | Newth et al. | 606/204 |
| 5,016,617 | 5/1991 | Tarlow et al. | 601/117 |
| 5,024,215 | 6/1991 | Wang | 128/75 |
| 5,094,227 | 3/1992 | Eglauf et al. | 128/60 |
| 5,097,823 | 3/1992 | Kempler | 128/60 |
| 5,184,606 | 2/1993 | Csorba | 128/28 |

*Primary Examiner*—Gary Jackson
*Assistant Examiner*—Scott B. Markow
*Attorney, Agent, or Firm*—Pearson & Pearson

[57] ABSTRACT

An apparatus for self administration of acupressure that comprises a surface for supporting the individual. A pressure arm supported above the surface moves between a first position displaced from the individual and a second position where pressure probes apply acupressure. The position of an actuation arm supported below the surface is controlled by the individual and is linked to the pressure arm. This enables the individual to control the magnitude and duration of force applied through the pressure arm and pressure probes. The individual can operate another linkage to position the pressure probes relative to the pressure arm and along the individuals' spine.

22 Claims, 4 Drawing Sheets

APPARATUS FOR APPLYING ACUPRESSURE

BACKGROUND OF THE INVENTION

1. Field of the Invention

This invention relates to the field of acupressure and more specifically to a method and apparatus for the self-administration of acupressure.

2. Description of Related Art

Healthy muscles are soft, flexible and well nourished by blood flow in the circulatory system. A decrease in the blood flow reduces the temperature of the muscle tissue and the oxygen and nutrient supply to the tissue. Muscles which are overworked or otherwise subjected to a reduction in temperature and in levels of oxygen and nutrients tend to become tense and painful. Conversely, increasing the blood flow to muscle tissue tends to reduce tension and pain in muscles exhibiting such conditions and reduce the likelihood of development of such conditions in other muscles. The application of acupressure at specific locations proximate the selected tissue increases the blood flow to selected muscle tissue. The application of such pressure is therefore useful in reducing and preventing muscle tension and pain resulting from reduced blood flow to the muscle tissue.

Generally, acupressure techniques require a second person to apply acupressure to muscle sites that are difficult to reach such as in the neck, shoulders, back, hip and buttocks. The requirement for another person can be relatively inconvenient as such a person is unavailable. Moreover, the costs of having a trained therapist or other professional apply pressure can become expensive and inconvenient particularly when frequent treatments are needed. Hand held pressure applying devices that activate or otherwise bear upon pressure points according to acupressure techniques are known. Examples of such devices are disclosed in the following U.S. Pat. Nos.:

4,037,590 (1977) Dohring et al.

5,094,227 (1992) Eglauf et al.

Other apparatus for the self-administration of acupressure includes a belt assembly disclosed by U.S. Pat. No. 4,716,898(1988) to Chauve et al. The belt, as it is drawn in about an individual, urges a pressure member extending radially inward from the belt into contact with a pressure point.

U.S. Pat. No. 4,944,747 (1990) to Newth et al. discloses a slightly curved elongated handle terminating in a flattened section with a rounded protrusion extending transversely therefrom and an eye hook at the tip of the section. A flexible strap passes through the eye hook, so that with the protrusion over a desired trigger point the individual pulls on the strap with one hand and levers the handle about the body to force the protrusion into the trigger point. This device, for effective use, requires prior knowledge to locate the appropriate points to apply pressure and requires the individual to have sufficient strength and flexibility in the arm and shoulders to operate the device.

U.S. Pat. No. 4,520,798 (1985) to Lewis discloses an arm that supports an outwardly extending bar at one end and that rotates at the other end on a plate mounted on a wall. A knob member removably attaches to the free end of the bar. To use this device, an individual positions the area to be treated in contact with the knob member and then pushes against the knob.

Further examples of apparatus for providing massage and acupressure are disclosed generally in the following patents:

3,403,674 (1968) Alimanestiano 3,799,155 (1974) Gerlich 4,352,491 (1982) Bellia 4,662,363 (1987) Romano et al.

4,924,859 (1990) Pajevic 5,024,215 (1991) Wang 5,097,823 (1992) Kempler

Alimanestiano discloses a massaging machine that comprises a frame supporting for a carriage for movement over an individual disposed on the frame. The carriage mounts hand elements thereon so that a motor carried by the frame actuates the carriage and the hand elements to provide a massaging action along the individual's body.

Gerlich discloses a massaging device comprising a substantially planar surface supported for transverse movement above an individual to be massaged. The surface has a plurality of massaging elements suspended therefrom for contacting the individual. A motorized unit reciprocates the surface relative to the individual to provide a massaging action.

Bellia discloses an exercise table having a semi-rigid support base supported for transverse rotation, two elongated rotational tubular members extending away from the base along the rotational axis of the base, and a rigid cushion disposed between the support base and the tubular members. The rigid cushion includes resilient spheres rotationally mounted therein. An individual sits on the semi-rigid support base with selected portions of the neck and back disposed between the resilient spheres. Then the individual then rocks the support base to apply varying pressure on the portions of the body supported on the spheres.

Romano et al. disclose a device that comprises a plurality of acupressure probes positioned within a frame for contacting an individual on a support surface. Each probe is adjusted to conform to the contours of the individual disposed under the probes. In use a second person bears down on the probe to apply the proper pressure and then locks the probe in place. While the device disclosed by Romano et al. allows the second person to see and do other things, the individual is "pinned" to the support surface until the second person returns. Additionally, the individual has no control over the treatment.

Pajevic discloses a body stimulating and massaging device comprising a plurality of spheroidal silicon rubber members secured along a cable supported in a serpentine fashion between a plurality of pulleys. The ends of the cable attach to a reciprocating motor through a shock absorbing tension assembly. The motor causes the spheroidal members to be drawn back and forth along a body disposed on top of them.

Wang discloses a back rack for alleviating musculoskeletal tension that includes a ramp with a pair of curved projections at its upper end to apply pressure to an individual's neck and skeletal areas. Levers connected to a supporting base of the ramp move from a vertical position to apply pressure and relieve tension in the shoulders. Pins inserted in the ramp proximate the neck and feet to relieve tension in the feet and neck.

Kempler discloses a device for applying a mechanical massage to a patient oriented in a horizontal position. An inner carriage mounts for movement in tracks within an outer cage by a motor driven crank. A motor driven crankshaft raises above a patient and then releases horizontally-mounted levers or massage arms to drop by gravity onto the individual as the inner carriage moves to simulate a massage. This device does not enable an individual to control the duration, location and force applied to a selected area.

The foregoing references disclose devices for applying acupressure in the neck, back, buttocks and other sites that are difficult to reach. However, the foregoing references fail to provide a relatively simple apparatus suitable for the self-administration of acupressure to such areas.

SUMMARY

An object of the present invention is to provide a device that enables an individual to self-administer acupressure.

Another object of the present invention is to provide an acupressure device that is simple for inexperienced individuals to use and operate effectively.

Still another object of the present invention is to provide an acupressure apparatus that is relatively simple and inexpensive to manufacture.

Still yet another object of the present invention is to provide a device that enables an individual to self-stimulate a plurality of acupressure points located on the neck, shoulders, back, hips and buttocks in succession without repositioning and to do so efficiently.

Yet a further object of the present invention is to provide an acupressure apparatus which allows an individual to control simply and effectively the location, duration, and force of acupressure.

In accordance with this invention, the above objects are attained by an apparatus comprising an acupressure structure that applies pressure to the individual. A frame supports the individual in a predetermined position. A pressure arm supported on the frame and attached to the acupressure structure enables the individual to move the pressure arm from a first position to a second position thereby to apply pressure to a predetermined acupressure point.

According to another aspect of the present invention an apparatus for applying pressure at a predetermined point comprises a frame including a chest supporting unit that locates the back in a predetermined orientation facing an acupressure arm. The frame supports the acupressure arm for movement between first and second positions spaced from the chest support unit. An actuator arm connected to the frame and the acupressure arm moves the acupressure arm from the first and second positions in response to movement of the actuator arm by the individual whereby the acupressure arm moves to the second position and applies pressure to the acupressure point on the individual's back.

According to a further aspect of the present invention an apparatus for enabling an individual to self-administer acupressure comprises a support system including a support surface for supporting the individual. An actuating member is disposed to one side of the support surface for movement by the individual. A pressure member is supported to the other side of the support surface for movement substantially perpendicular to the support surface. It interconnects with the actuating member. Moving the actuating member in a first direction causes the pressure member to engage the individual and apply a force to the individual. Moving the actuating member in a second direction relieves the force applied to and disengages the pressure member from the individual.

According to still a further aspect of the present invention an apparatus for enabling an individual to self-administer acupressure comprises a support system including a base for mounting on a horizontal surface and a support surface for supporting the individual on the apparatus. A pressure application system enables the individual on the support surface to apply pressure to a preselected area. The pressure application assembly comprises an actuating member disposed below the support surface for manipulation by the individual and a pressure member supported above the support surface for movement substantially perpendicular to that support surface. The actuation member and the pressure member interconnect such that movement of the actuating member in a first direction toward the base urges the engagement of the pressure member against the individual to apply acupressure. Movement of the actuating member in a second direction away from the base reduces the force applied to the individual and displaces the pressure member from the individual.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
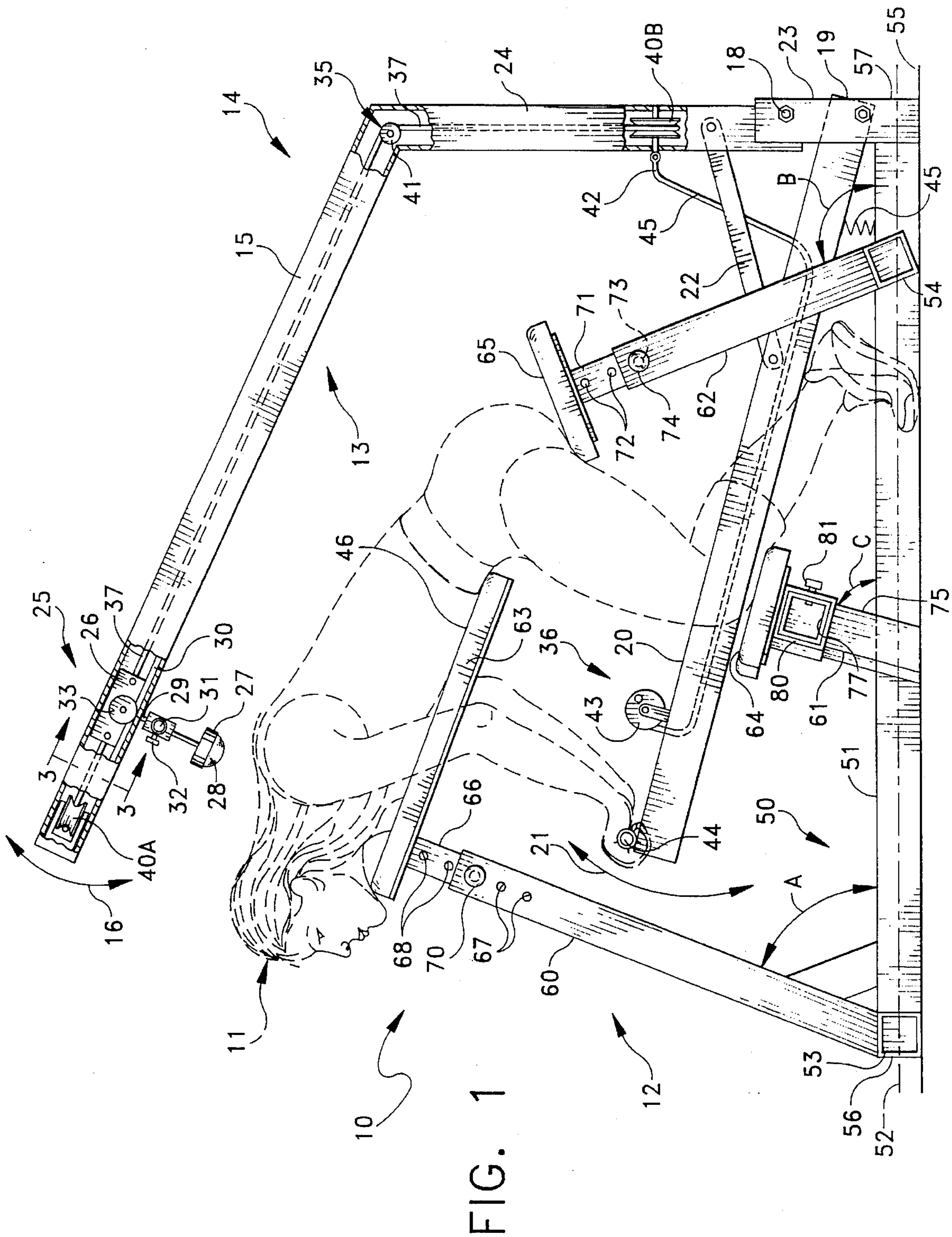
FIG. 1 is a side elevational view with portions cut-away of apparatus constructed in accordance with this invention.
Figure 2:
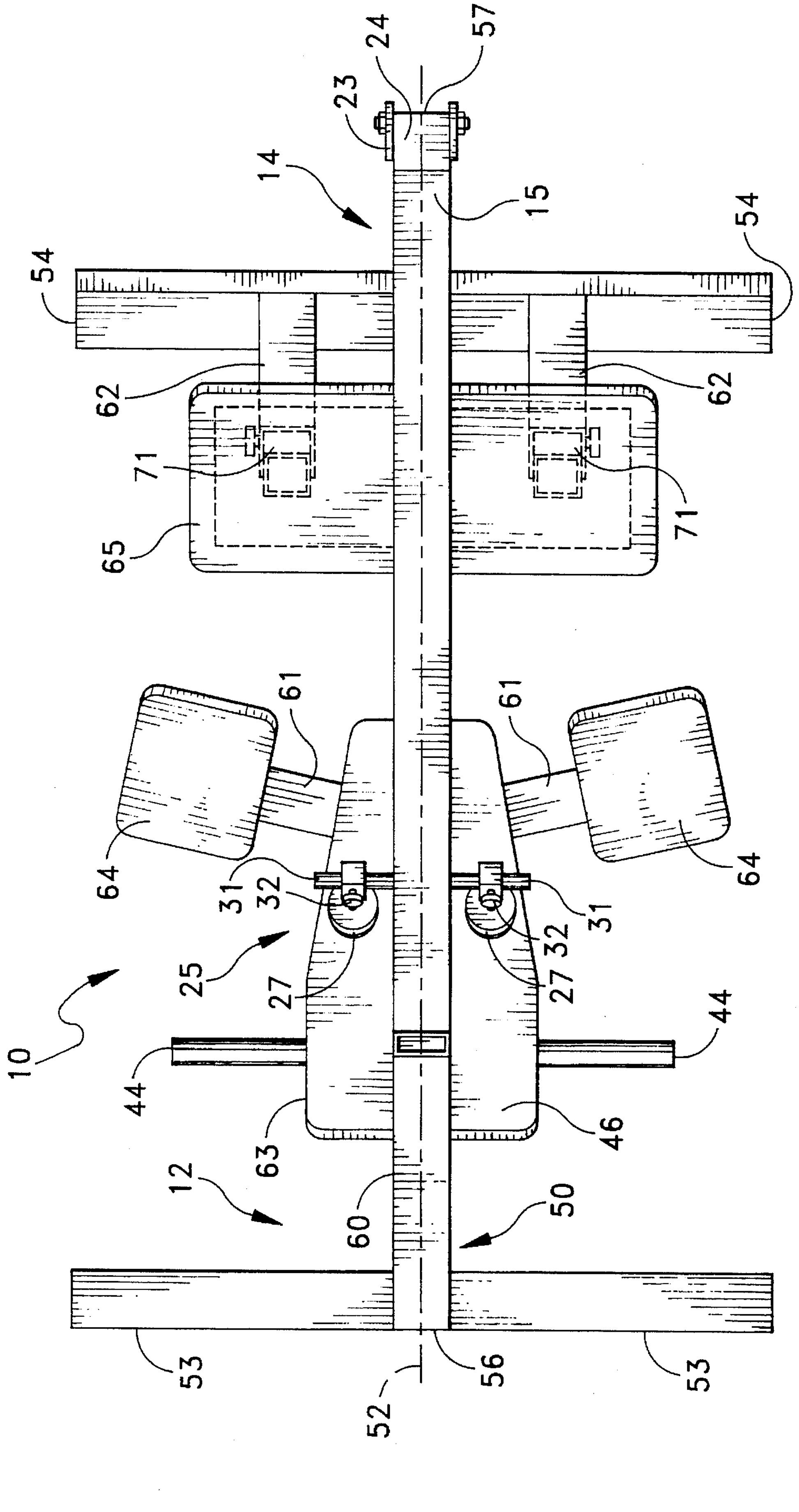
FIG. 2 is a top elevational view of the apparatus of FIG. 1.

FIGS. 1 and 2 depict apparatus 10 according to the present invention that enables an individual 11 to self-administer acupressure at various acupressure points. The apparatus 10 comprises generally a support system 12 for supporting the individual 11 and a pressure application system 13 for applying acupressure. The pressure application system 13 includes a pressure member 14 with a pressure arm 15 that pivots on the support system 12 in the directions indicated by arrow 16. An actuating member 20 that is also a component of the pressure application assembly 13, that pivots on the support system 12 in the direction of the arrows 21. A linkage 22 interconnects the actuation arm 20 and the pressure arm 15. In this specific embodiment the pressure member 14 and the actuating arm 20 rotate at pivots 18 and 19 respectively formed in upstanding brackets 23 formed at one end of the support system 12. If the individual 11 and actuation arm 20 are positioned as shown in FIG. 1 and the individual displaces the actuation member 20 downward, the pressure arm 15 displaces downwardly due to the linkage 22. This relationship between the pressure member 14 and the actuation arm 20 enables the individual 11 to control the magnitude and the duration of the force applied to an acupressure point.

Figure 3:
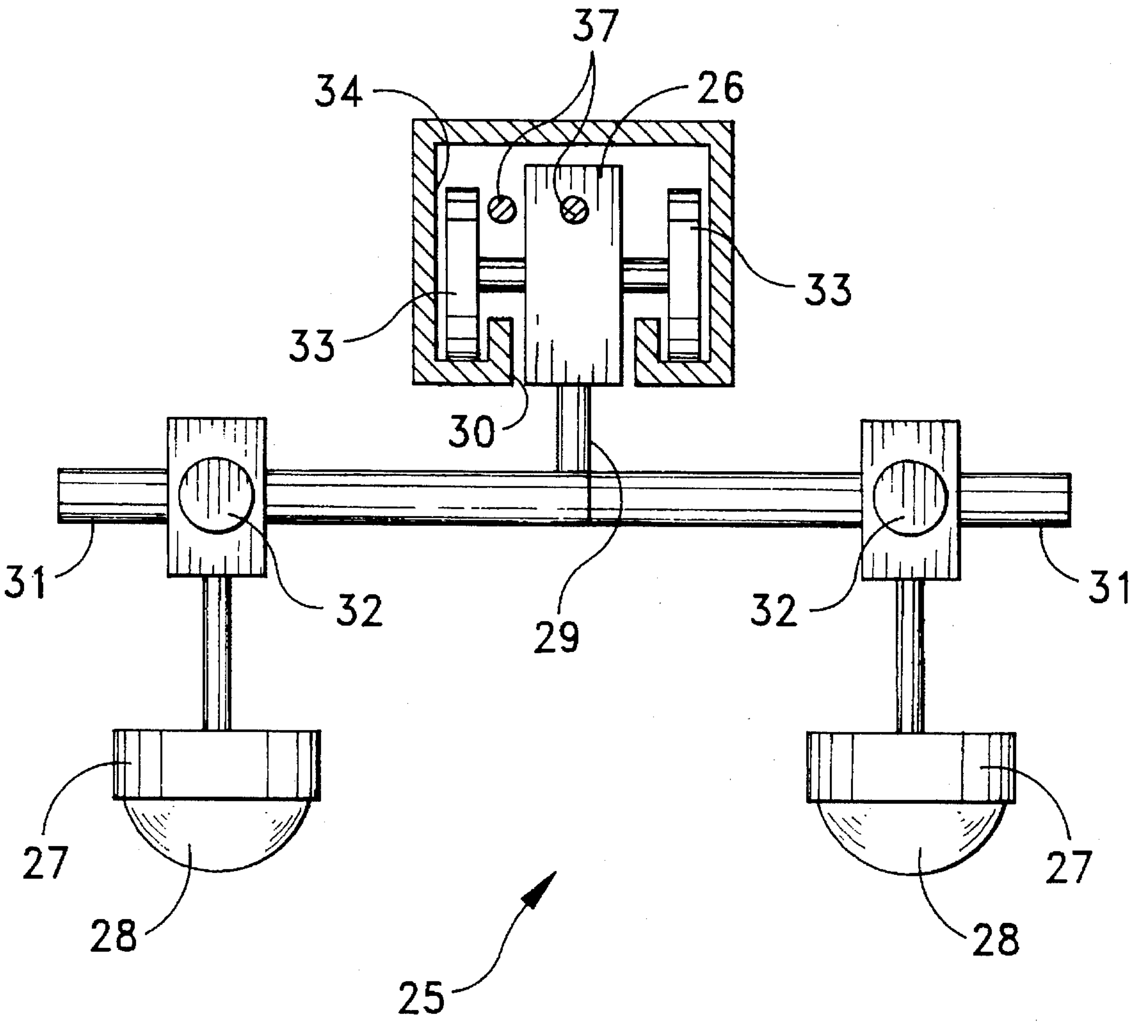
FIG. 3 is a sectional view taken along lines 3—3 of FIG. 1.

Referring now to FIGS. 1 and 3, the pressure member 14 additionally includes an interconnecting arm 24 that attaches at one end to pivot 18. The pressure arm 15 cantilevers from the other end. The pressure member 14 further comprises an acupressure structure 25 that can slide along the pressure arm 15. The acupressure structure 25 includes a carriage 26 and pressure probes 27, preferably formed with hemispherical surfaces 28. Specifically a T-shaped support element 29 extends through an elongated aperture 30 in the pressure arm 15. Arms 31 that extend laterally from the element 28 carry the pressure probes 27. A friction locking screw 32, or similar device, enables an individual 11 to adjust the angular orientation and the lateral position of the pressure probes 27 relative to the pressure arm 15.

Continuing to refer to FIGS. 1 and 3, wheels 33 mounted on the carriage 26 enable the movement of the carriage 26 within an internal track 34 along the longitudinal axis of the pressure arm 15. A pulley and cable system 35 connected to a manual drive system 36 enables the user to control the position of the carriage 26. Specifically, a cable 37 attaches to the carriage 26 and wraps around an end pulley 40A at the free end of the pressure arm 15 and a pulley 40B in the interconnecting arm 24 proximate the linkage 22. An intermediate idler pulley 41 is located at the juncture of the interconnecting arm 24 and the pressure arm 15. Pulley wheel 40B includes a positive drive connection with the cable 37 so moving the pulley wheel 40B displaces the carriage 26. More specifically a drive cable 42 connects at one end to the pulley 40B and at the other end to a crank 43 or other operator mounted for rotation preferably on the actuation arm 20. This enables an individual 11 to rotate the crank 43 and position the carriage 26 and the pressure probes 27 along the pressure arm 15.

As previously indicated with reference to FIGS. 1 and 2, the actuation arm 20 attaches to the pivot 18 at a location of the bracket 23 below the pivot 18. Normally the attachment positions for the linkage 22 and the angle between the pressure arm 15 and the interconnecting arm 24 are selected so the pressure arm 15 and the actuation arm are nearly parallel. The angle of the actuation arm 20 from a horizontal position, in the context of FIG. 1, is selected so that an individual can readily grasp handles 44 that extend transversely from the actuation arm 24.

In many applications the pressure application system 13 will have sufficient friction to stabilize the pressure member 14 and activation arm 20 in any operable position. In other applications a spring 45 intermediate the support system 12 and the actuation arm 20 may bias the actuation arm 20 and pressure arm 15 into a position as shown in FIG. 1 wherein the pressure arm 15 is spaced above a support surface 46.

With this orientation, it is relatively easy for an individual 11 to assume the position shown in FIG. 1. As the individual 11 pushes the actuation arm 20 downwardly against the bias of the spring 45, the pressure arm 15 moves the pressure probes 27 into contact the individual's back. The individual 11 then can operate the crank 43 to position the pressure probes 27 along the back to an appropriate position. The force exerted on the actuation arm 20 directly relates to the force applied to the individual's back by the pressure probes 27 so the individual 11 has control over that force and its duration.

Continuing to refer to FIGS. 1 and 2, the support system 12 includes a frame 50 preferably formed of rectangular metal tubing and generally formed for mounting on a floor or other horizontal surface. An elongated central member 51 along a central axis 52 carries transverse leg members 53 and 54 that contact a floor 55 or other support surface proximate opposite ends 56 and 57 of the central member 51 for stability. The leg members 53 and 54 act as outriggers that contact the floor 55.

The frame 50 also includes support tubes 60, 61 and 62 extending generally upwardly from the central member 51 and the leg member 54. These tubes carry a table 63 that defines the support surface 46, knee pads 64 and a seat 65, respectively. The tube 60 extends from the end 57 of the central member 51 at an acute angle "A" that is typically fixed. The chest supporting surface 46 is fixed to a similar, but smaller sized tubular member 66 that nests within the support tube 60. An aperture 67 extends through opposed walls of the tube 60. The tubular member 66 includes a plurality of similarly sized apertures 68 that register, respectively, with the apertures 67 as the tubular member 66 moves relative to the tube 60. A locking pin 70 passes through the aperture 67 and a registered one of the apertures 68 to lock the support surface 46 in a selected position. This structure allows the individual 11 to adjust the height of the support surface 46 for comfort.

Parallel support tubes 62 disposed on opposite sides of the actuator arm 20 extend at an obtuse angle B relative to the central axis 52 from the leg member 54. The support tubes 62 receive tubes 71 that carry the seat 65. Each of the tubes 71 includes a plurality of apertures 72 that register with an aperture 73 in each of the support tubes 62, as the tubes 71 move relative to the tubes 62. A pin 74 extends through those of apertures 72 in register with the apertures 73 in each of the support tubes 62 to fix the height of the seal 65 relative to the frame 50. This structure allows the individual 11 to adjust the height of the seat 65 in comfort.

Each of the support tubes 61 comprises an inverted L-shaped member 75 and a spacer member (not shown), that is secured at one end to the central member 51. In the side elevation shown in FIG. 1, the support tube lies an acute angle C relative to the axis 52. Each lateral extension 77 receives an oversized tube 80 that carries a knee pad 64. A friction locking screw 81 enables the individual 11 to position the knee pads 63 at a comfortable position.

To use the apparatus 10, the individual 11 positions the support table 63, knee pads 64 and seat 65 appropriately and orients and positions the pressure probes 27. The individual 11 then moves into the position shown in FIG. 1. Initially the individual 11 moves the actuation arm 20 downwardly to bring the bearing surfaces 28 into light contact with his or her body. Any required adjustment parallel to the spine can be made by operating the crank 43. Then the individual 11 exerts a greater downward force on the actuation arm 20 until the bearing surfaces 28 exert appropriate pressure at the selected acupressure point. The individual 11 completely controls the magnitude and duration of this force or acupressure. Generally the spacing between pressure points at different spinal positions is constant, so the individual may apply acupressure at different sites merely by using the crank 43. At other times the individual may have to exit the apparatus 10 to adjust the location of the pressure probes 27 in the carriage 26.

Figure 4:
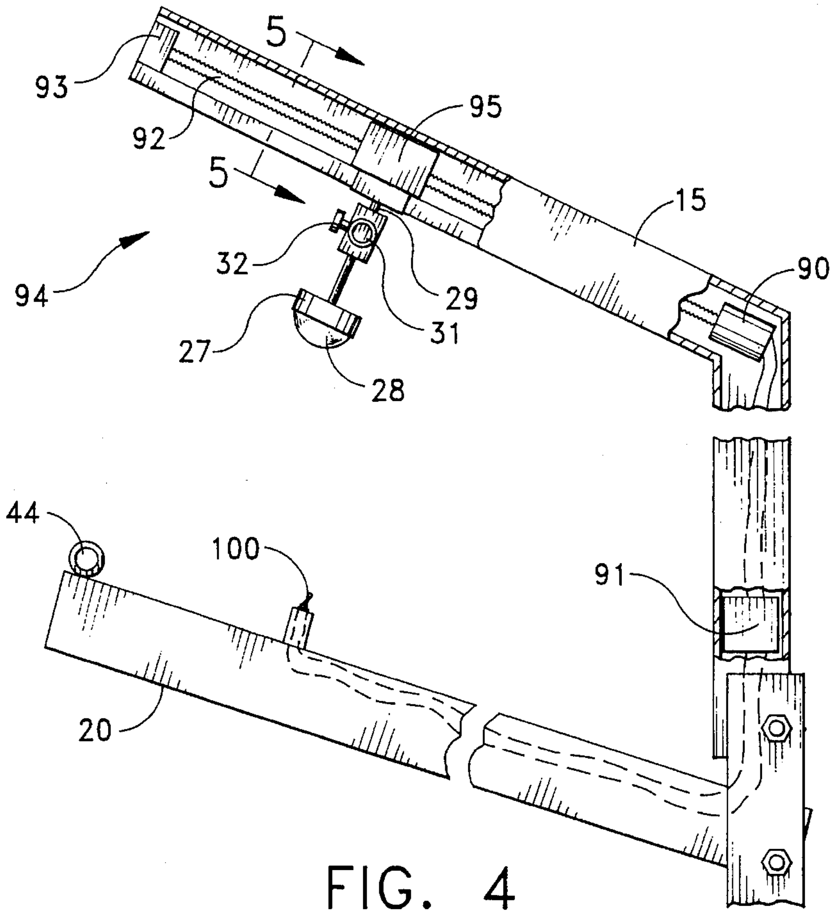
FIG. 4 is a partial side elevational, partial diagrammatic view of a portion of another embodiment of the apparatus according to this invention.
Figure 5:
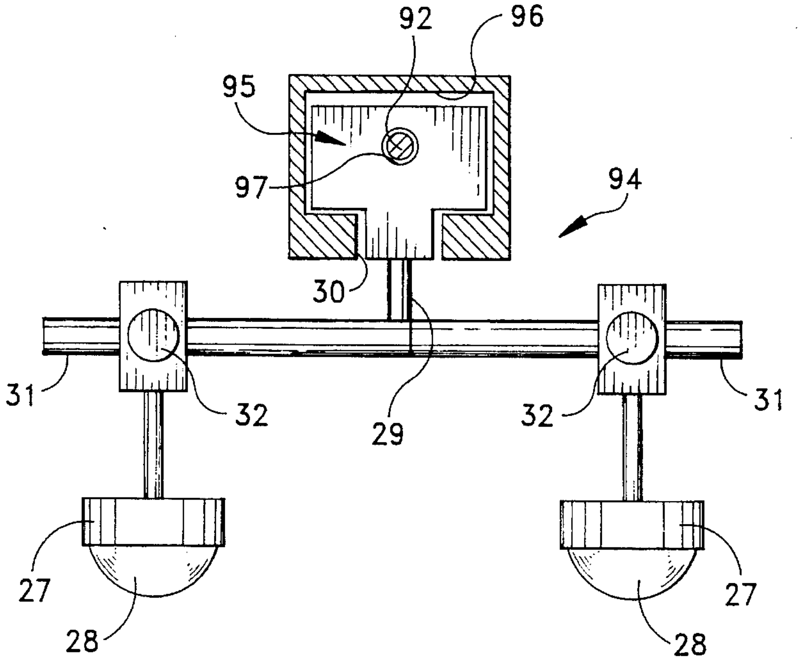
FIG. 5 is a sectional view taken along lines 5—5 of FIG. 4.

FIGS. 4 and 5 depict an alternative embodiment of the present invention that includes a reversible motor 90 connected to a power supply 91 for rotating a threaded lead screw 92. One end of the lead screw 92 attaches to the motor 90. The lead screw 92 extends axially through the pressure arm 15. A mount 93 at the free end of the pressure arm 15 supports the other end of the lead screw 92. An acupressure structure 94, similar to the acupressure structure 25 of FIG. 1, includes a carriage 95 within an internal track 96 of the pressure arm 15. The track 96 and the carriage 95 are provided with closely spaced opposed surfaces that function as bearing surfaces. The lead screw 92 extends through and engages corresponding threads of a central aperture 97 of the carriage 95 so that rotation of the lead screw 92 displaces the carriage 95 linearly along the arm.

A control switch 100 preferably positioned on the actuating arm 20 enables the user to selectively actuate the motor and, thus, remotely control the position of the carriage along the pressure arm. Additionally, by placing the switch near, on or in the handle 44 the user can with relative ease provide a self-administered massage by holding the actuation arm 20 in an active position and then selectively toggling the control switch 100 between forward and reverse positions to cause the carriage 95 and thus the probes 27 to move along the pressure arm 15 while maintaining contact with individual's back.

Therefore, the present invention provides an apparatus suitable for the self-administration of acupressure. The apparatus is simple to use and can apply acupressure in diverse locations including areas of the neck, back and buttocks that do not lend themselves to the self-administration of acupressure. This invention has been disclosed in terms of a specific embodiment. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. Acupressure apparatus for applying acupressure to an individual at a predetermined acupressure point, said apparatus comprising:

(A) acupressure means for engaging the individual at the acupressure point, (B) frame means for supporting an individual in a predetermined position wherein the individual is spaced from said acupressure means when said acupressure means is in a first position, (C) pressure arm means supported on said frame means and attached to said acupressure means for moving said acupressure means between the first position spaced from the individual and a second position wherein said acupressure means contacts and applies acupressure at the acupressure point, and (D) actuation arm means supported on said frame means and connected to said pressure arm means for urging, responsive to a force applied to said actuation arm means by the individual, said pressure arm means to move said acupressure means from the first position to the second position and for transferring a force, proportional to the force applied by the individual, through said pressure arm means and said accpressure arm means to the individual when said acupressure means contacts the acupressure point.

2. Acupressure apparatus as recited in claim 1 wherein there exists a plurality of acupressure points on the individual, wherein said acupressure apparatus additionally includes position control means for aligning said acupressure means with each of the plurality of acupressure points by controlling the position of said acupressure means for selective linear motion with respect to said pressure arm means.

3. Acupressure apparatus as recited in claim 2 wherein said frame means includes means for supporting the individual's chest and a first end of said actuation arm means attaches to said frame means and said pressure arm means and a second end of said actuation arm means includes a handle portion proximate to said chest support means.

4. Acupressure apparatus as recited in claim 3 wherein said position control means includes operator means mounted adjacent said handle portion for manipulation by the individual to align said acupressure means and means for converting motion of said operator means into the linear motion of said acupressure means along said pressure arm means whereby the individual can move the acupressure means into alignment with each of the plurality of acupressure points.

5. Acupressure apparatus as recited in claim 3 wherein said acupressure means includes a body portion in said pressure arm means and said position control means includes a crank attached to said handle portion for rotation relative thereto by the individual and cable linkage means supported by said actuation arm means and said frame means for interconnecting said crank and said acupressure means body portion whereby rotation of said crank by the individual moves the acupressure means with respect to said pressure arm means.

6. Acupressure apparatus as recited in claim 3 wherein said acupressure means includes a body portion in said pressure arm means and said position control means includes a motor selectively controlled by the individual and a lead screw rotatably supported in said pressure arm means and operatively connected to said motor for rotary motion, said lead screw threadably engaging said body portion, whereby activation of said motor by the individual urges the movement of said acupressure means along said lead screw with respect to said pressure arm means.

7. Acupressure apparatus as recited in claim 6 wherein said position control means further includes a switch supported by said frame means proximate the individual for activating said motor to move said acupressure means with respect to said pressure arm means when in said second position to enable the individual to self-administer a massage to selected areas of the individual's body.

8. Acupressure apparatus as recited in claim 1 wherein said pressure arm means includes a first arm pivotally mounted on said frame means and a pressure arm extending from the first arm and said actuation arm means includes an actuator arm pivotally secured at one end to said frame means with handles at a second end thereof and a link connecting said first arm and said actuator arm.

9. Acupressure apparatus as recited in claim 8 wherein said frame means includes a base for supporting said apparatus on a surface.

10. Acupressure apparatus as recited in claim 9 wherein the frame means includes a table, seat and knee supports.

11. Acupressure apparatus as recited in claim 1 wherein said acupressure means includes a body for being supported by said pressure arm means and an element depending from said body and forming at least a portion of a spherical surface for engaging the individual at the acupressure point.

12. Acupressure apparatus as recited in claim 1 wherein said acupressure means includes a body for being supported on said pressure arm means and first and second elements each of which depends from said body and forms at least a portion of a spherical surface for engaging the individual at first and second acupressure points.

13. Acupressure apparatus as recited in claim 12 wherein said acupressure means includes means for positioning said first and second elements with respect to said pressure arm means.

14. Acupressure apparatus for providing pressure to an individual at a predetermined acupressure point, said apparatus comprising:

(A) a frame including a chest supporting unit for supporting the individual's chest such that the back is located in a predetermined orientation;

(B) an acupressure arm supported by said frame, said acupressure arm including an acupressure portion with said acupressure arm being moveable between a first position with said acupressure portion relatively widely spaced from said chest support unit and a second position with said acupressure portion engaging the individual supported by said support unit; and (C) an actuator arm supported by said frame and linked to said acupressure arm, said actuator arm responsive to a force applied by the individual being moveable between third and fourth positions to urge movement of said acupressure arm between the first and second positions, respectively, whereby said acupressure portion when in the second position applies pressure to the acupressure point on the individual's back proportional to the force applied to said actuator arm by the individual.

15. An apparatus as recited in claim 14 wherein said frame further includes a knee receiving platform for supporting the individual's knee.

16. An apparatus as recited in claim 15 wherein said frame further includes a seat portion.

17. Apparatus for enabling an individual to self administer acupressure, said apparatus comprising:

(A) a frame;

(B) support means connected with the frame for supporting the individual, said support means includes a support surface with an upper surface area for engaging the individual and a lower surface area;

(C) an actuating member means supported by said frame below said support surface for movement by the individual from a first to a second position responsive to a force applied to said actuating member means by the individual; and (D) a pressure member means supported by said frame above said support surface to overlie said upper surface area and mechanically linked with said actuating member means for moving substantially perpendicular to said upper surface area to engage the individual responsive to movement of said actuating means to the second position, said pressure member means being further adapted for applying a force upon engagement with the individual proportional to the force applied by the individual to said actuating member means when in the second position.

18. An apparatus according to claim 17 wherein said pressure member means comprises an arm pivotally supported by said frame and a carriage movably carried by said pivotally supported arm for selective position along said pivotally supported arm.

19. An apparatus according to claim 18 further comprising a drive means supported by said frame and connecting with said carriage for enabling the individual to move said carriage along said pivotally supported arm wherein said pressure member means further includes a plurality of pressure probes mounted on said carriage for contacting the individual.

20. An apparatus for enabling an individual to self-administer acupressure, said apparatus comprising:

(A) support system including a base for mounting on a horizontal surface and a support surface spaced above and supported by said base, said support surface adapted for supporting the individual on said apparatus;

(B) a pressure application system for enabling the individual on said support system to apply pressure to a preselected area on the individual including actuating member means connected to said base and disposed below said support surface for manipulation by the individual and a pressure member means supported above the support surface by said base for movement substantially perpendicular to the support surface, said actuated member means and said pressure member means being interconnected such that application of a force to move said actuating member means in a first direction urges said pressure member into engagement with the individual and to apply a pressure to the individual proportional to the force and movement of said actuating member in a second direction reduces the force applied to the individual and tends to displace said pressure member away from he individual.

21. An apparatus as recited in claim 20 wherein said pressure member means comprises arm means pivotally supported from said base for pivotal movement in a vertical plane toward and away from said support surface and a pressure assembly carried by said arm means at selectable positions thereon.

22. An apparatus as recited in claim 21 wherein said pressure assembly includes a pressure probe for engaging the individual and amount carried by the arm means and adjustably attaching the pressure probe to said arm means whereby the position of said pressure probe relative to said arm means can be altered.

* * * * *